United States Patent [19]
Gaffar et al.

[11] Patent Number: 6,110,445
[45] Date of Patent: Aug. 29, 2000

[54] ORAL COMPOSITION EXHIBITING IMPROVED UPTAKE AND RETENTION OF ANTIBACTERIAL COMPOUNDS ON DENTAL TISSUE SURFACES

[75] Inventors: Abdul Gaffar, Princeton; Nuran Nabi, Cranbury, both of N.J.

[73] Assignee: Colgate-Palmotive Company, New York, N.Y.

[21] Appl. No.: 09/181,892

[22] Filed: Oct. 29, 1998

Related U.S. Application Data

[63] Continuation-in-part of application No. 08/808,607, Feb. 28, 1997, abandoned, which is a continuation-in-part of application No. 08/494,744, Jun. 26, 1995, Pat. No. 5,605,676.

[51] Int. Cl.[7] .................. A61K 7/16; A61K 7/18
[52] U.S. Cl. .................. 424/49; 424/52; 424/57
[58] Field of Search .................. 424/49–58

[56] References Cited

U.S. PATENT DOCUMENTS

| | | |
|---|---|---|
| 4,139,485 | 2/1979 | Imokawa et al. . |
| 4,152,421 | 5/1979 | Tsutsumi et al. . |
| 4,350,680 | 9/1982 | Harvey et al. . |
| 4,358,437 | 11/1982 | Duke . |
| 5,019,373 | 5/1991 | Carter et al. . |
| 5,605,676 | 2/1997 | Gaffar et al. . |

FOREIGN PATENT DOCUMENTS 6271440  9/1994  Japan .

OTHER PUBLICATIONS

*International Dental Journal*, vol. 44, Issue No. 1, Supplement 1 (1994), by Gaffar et al.

*Primary Examiner*—Shep K. Rose
*Attorney, Agent, or Firm*—Henry S. Goldfine

[57] ABSTRACT

The invention provides an antibacterial oral composition containing an antibacterial compound, a monoalkyl phosphate compound and another anionic surfactant; whereby, the antibacterial effect on dental tissue is substantially increased due to the combined presence of the monoalkyl phosphate compound and the other anionic surfactant in a given weight ratio.

20 Claims, No Drawings

ORAL COMPOSITION EXHIBITING IMPROVED UPTAKE AND RETENTION OF ANTIBACTERIAL COMPOUNDS ON DENTAL TISSUE SURFACES

CROSS-REFERENCE TO RELATED APPLICATIONS

This is a continuation-in-part of application Ser. No. 08/808,607, filed Feb. 28, 1997, now abandoned which is a continuation-in-part of application Ser. No. 08/494,744, filed Jun. 26, 1995, now U.S. Pat. No. 5,605,676, granted Feb. 25, 1997.

BACKGROUND OF THE INVENTION

1. Field of the Invention

The present invention relates to oral care compositions which are designed to improve the effectiveness of antibacterial compounds in the retardation and prevention of bacterial plaque accumulation on the teeth.

2. The Prior Art

Dental plaque is a soft deposit which forms on teeth and is comprised of an accumulation of bacteria and bacterial by-products. Plaque adheres tenaciously at the points of irregularity or discontinuity, e.g., on rough calculus surfaces, at the gum line and the like. Besides being unsightly, plaque is implicated in the occurrence of gingivitis and other forms of periodontal disease.

A wide variety of antibacterial agents have been suggested in the art to retard plaque formation and the oral infections and dental disease associated with plaque formation. For example, halogenated hydroxydiphenyl ether compounds such as triclosan are well known to the art for their antibacterial activity and have been used in oral compositions to counter plaque formation by bacterial accumulation in the oral cavity.

Although antibacterial agents such as triclosan are highly effective in killing bacteria which are responsible for plaque formation, it is difficult to maintain an effective level of such agents on dental tissue for a significant time period after their application. Thus, once applied, it is important that the antibacterial compound be maintained in continuing adherence to the teeth and adjacent oral gingival mucosa thereby retarding washout of the antibacterial compound from infected areas of dental tissue by saliva present in the mouth. This allows for a sufficient amount of compound to remain in contact with the dental tissue and achieve a protracted and therefore enhanced antibacterial effect.

SUMMARY OF THE INVENTION

U.S. Pat. No. 5,605,676 discloses that the presence of relatively low concentrations, e.g., about 0.1 to about 5% by weight, of a monoalkyl phosphate compound, substantially free of any other alkyl phosphate compound, in an oral composition containing an antibacterial halogenated diphenyl ether or phenolic compound substantially increases uptake and retention of the antibacterial compound on dental tissue. Unexpectedly, it has been discovered that when an anionic surfactant, other than an alkyl phosphate, is also present in the oral composition and the weight ratio of the anionic surfactant to monoalkyl phosphate ranges from about 2:1 to about 1:2, the antibacterial efficacy of the composition is materially enhanced.

DETAILED DESCRIPTION OF THE PREFERRED EMBODIMENTS

The term "oral composition" is used herein to designate products which, in the ordinary course of usage, are retained in the oral cavity for a time sufficient to contact substantially all of the dental surfaces but are not intentionally ingested. Such products include, for example, dentifrices, gels, mouthwashes, chewing gums and lozenges.

Halogenated diphenyl ether antibacterial compounds for use in the oral care compositions of the present invention particularly desirable from considerations of antiplaque effectiveness and safety include 2,4,4'-trichloro-2'-hydroxy-diphenyl ether (triclosan) and 2,2'-dihydroxy-5,5'-dibromo-diphenyl ether.

Phenolic compounds useful in the practice of the present invention include phenol and its homologs, mono and polyalkyl and aromatic halophenols, resorcinol and its derivatives and bisphenolic compounds, such phenolic compounds being more fully disclosed in U.S. Pat. No. 5,368,844 the disclosure of which is incorporated herein by reference. Preferred phenolic compounds are n-hexyl resorcinol and 2,2'-methylene bis (4-chloro-6-bromophenol).

The halogenated diphenyl ether or phenolic antibacterial compound is present in the oral composition of the present invention in an effective antiplaque amount, typically about 0.05%–2.0% by weight, and preferably about 0.1%–1% by weight of the oral composition.

The term "monoalkyl phosphate compound" includes within its meaning a monoalkyl or monoalkenyl phosphate, mixtures thereof, and a salt thereof having the formula:

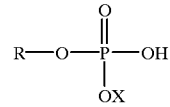

wherein R is an alkyl or alkenyl group having 6 to 18 carbon atoms and X is hydrogen sodium, potassium or ammonium and wherein the monoalkyl phosphate compound is substantially free of any other alkyl phosphate compound.

Monoalkyl phosphate compounds useful in the practice of the present invention include monolauryl phosphate, monooctyl phosphate, sodium lauryl phosphate and sodium monooctyl phosphate. A preferred monolauryl phosphate, which is substantially free of any other alkyl phosphate compound, is manufactured by Kao Corporation under the trade designation MAP-20H, and available from High Point Chemical Corporation, High Point, N.C. 27261.

Monoalkyl phosphate compounds are known to the art and used in combination with dialkyl phosphates in skin care compositions, e.g., U.S. Pat. No. 4,139,485, and as anionic surfactants (U.S. Pat. No. 4,139,485, U.S. Pat. Nos. 4,152, 421 and 4,350,680). Combinations of mono- and dialkyl phosphate salt have been disclosed as having efficacy as anti-caries agents (U.S. Pat. No. 5,019,373). Japanese Patent 6271440 discloses an antimicrobial compound of the formula Am+ Xm– wherein Am+ is a nitrogen containing antimicrobial agent and X– is an 8 to 20 carbon monoalkyl or monoalkenyl phosphoric acid ion and m is the valence of cation A. There is no suggestion in the prior art that oral compositions containing monoalkyl phosphate compounds, as the sole alkyl phosphates, used in combination with another anionic surfactant and an antibacterial compound would have an enhanced antibacterial effect.

Examples of anionic surfactants suitable for use in the practice of the present invention include water-soluble salts of higher fatty acid monoglyceride monosulfates, such as the sodium salt of the monosulfated monoglyceride of hydrogenated coconut oil fatty acids, higher alkyl sulfates, such as sodium lauryl sulfate, alkyl aryl sulfonates, such as sodium dodecyl benzene sulfonate, higher alkyl sulfoacetates, higher fatty acid esters of 1,2-dihydroxypropane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl, or N-palmitoyl sarcosine which should be substantially free from soap or similar higher fatty acid material. A preferred anionic surfactant is sodium lauryl sulfate.

The combination of a monoalkyl phosphate compound and another anionic surfactant, substantially free of any other alkyl phosphate compound, is found to significantly enhance the antibacterial effect of halogenated diphenyl ether and phenolic antibacterial compounds on dental tissue when the monoalkyl phosphate and the other anionic surfactant are incorporated in the oral composition in amounts effective to achieve such enhancement, such amounts being within the range of about 0.1 to about 5% of each ingredient by weight within the oral composition, preferably about 0.2% to about 3%, and most preferably about 0.3% to about 1.2% by weight of each ingredient within the oral composition, the weight ratio of the other anionic surfactant to monoalkyl phosphate ranging from about 2:1 to about 1:2.

In the preparation of an oral care composition in accordance with the practice of the present invention, an orally acceptable vehicle including a water-phase with humectant is present. The humectant is preferably glycerine, sorbitol, and/or propylene glycol. Water is present typically in amount of at least about 10% by weight, generally about 25 to 70% by weight and the humectant concentration typically totals about 10–80% by weight of the oral composition.

Dentifrice compositions also typically contain polishing materials including crystalline silica, having a particle size of up to about 20 microns, such as available as Zeodent 115, silica gel or colloidal silica, complex amorphous alkali metal aluminosilicates, as well as sodium bicarbonate, calcium carbonate, calcium pyrophosphate, dicalcium phosphate and alumina.

Dentifrices prepared in accordance with the present invention typically contain a natural or synthetic thickener in proportions of about 0.1 to about 5% by weight, preferably about 0.5 to about 2% by weight. Suitable thickeners include Irish moss, i-carrageenan, gum tragacanth, starch, polyvinylpyrrolidone, hydroxyethypropyl cellulose, hydroxybutyl methyl cellulose, hydroxypropyl methylcellulose, hydroxyethyl cellulose sodium carboxymethyl cellulose (NaCMC), and colloidal silica such as those available as finely ground Syloid 244 and Sylodent 15.

The oral composition may also contain a source of fluoride ions, or fluoride-providing compound, as an anticaries agent, in an amount sufficient to supply about 25 ppm to 5,000 ppm of fluoride ions and preferably 500 to 1500 ppm fluoride ions. Among these compounds are inorganic fluoride salts, such as soluble alkali metal salts, for example, sodium fluoride, potassium fluoride, sodium fluorosilicate, ammonium flourosilicate and sodium monofluorphosphate, as well as tin fluorides, such as stannous fluoride and stannous chloride.

Any suitable flavoring or sweetening material may also be employed. Examples of suitable flavoring constituents include flavoring oils, e.g. oil of spearmint, peppermint, wintergreen, clove, sage, eucalyptus, marjoram, cinnamon, lemon, and orange, and methyl salicylate. Suitable sweetening agents include sucrose, lactose, maltose, xylitol, sodium cyclamate, perillartine, AMP (aspartyl phenyl alanine methyl ester), saccharine and the like. Suitably, flavor and sweetening agents may each or together comprise from about 0.1% to 5% more of the oral care composition.

Various other materials may be incorporated in the oral preparations of this invention such as whitening agents, including urea peroxide, calcium peroxide, and hydrogen peroxide, preservatives, vitamins such as vitamin B6, B12, E and K, silicones, chlorophyll compounds, potassium salts for the treatment of dental hypersensitivity such as potassium nitrate as well as antitartar agents such as sodium tripolyphosphate and di- and tetraalkali metal pyrophosphate salts such as di- and tetrasodium pyrophosphate. These agents, when present, are incorporated in the compositions of the present invention in amounts which do not substantially adversely affect the properties and characteristics desired.

The preparation of dentifrices is well known in the art. U.S. Pat. Nos. 3,996,863, 3,980,767, 4,328,205, and 4,358,437, which are incorporated herein by reference, describe toothpastes and methods of production thereof, which may be utilized for production of the dentifrices according to the present invention. Further, discussion of the preparation of oral compositions is presented in Harry's Cosmeticology, Seventh Edition, 1982, edited by J. B. Wilkinson and R. J. Moore, published by Chemical Publishing of New York, pages 609 to 617. For example, to prepare a dentifrice of the present invention, generally humectants such as glycerin, propylene glycol, polyethylene glycol ingredients, are dispersed with a sweetener and water in a conventional mixer, until the mixture becomes a homogeneous gel phase. Into the gel phase are added a pigment such as $TiO_2$, any acid or base required to adjust the pH, and any fluoride anticaries agents, such as sodium fluoride. These ingredients are mixed until a homogenous phase is obtained, whereupon a polishing agent is mixed into the gel phase. The mixture is then transferred to a high speed/vacuum mixer; wherein, the thickener, such as gum, Sylodent 15 or sodium carboxymethyl cellulose; flavor; and surfactant ingredients, including the monoalkyl phosphate and another anionic surfactant such as sodium lauryl sulfate or sodium dodecyl benzene sulfonate are added and the resultant composition is then mixed at high speed under vacuum of from about 20 to 100 mm of Hg. The resultant product is in each case a homogeneous, semi-solid, extrudable paste product.

The following examples are further illustrative of the nature of the present invention, but it is understood that the invention is not limited thereto. All amounts and proportions referred to herein and in the appended claims are by weight, unless otherwise indicated.

EXAMPLE I

A liquid dentifrice of the present invention designated Composition A was prepared following the above discussed procedure containing 1.0% by weight monolauryl phosphate (MLP) and 0.5% by weight sodium lauryl sulfate (SLS), an anionic surfactant, the detailed formulation for which is shown in Table I. This composition was repeated a series of times as Compositions B, C, D, E, and F; these compositions differing from Composition A only in the relative quantities of monolauryl phosphate and sodium lauryl sulfate within each composition (q.s. water), as shown in Table II.

TABLE I

Liquid Dentifrice Formulation A

| Composition | A<br>Wt. % |
|---|---|
| Ingredients: | |
| Sorbitol | 20.00 |
| Glycerol | 20.00 |
| Propylene Glycol | 0.50 |
| Sodium Lauryl Sulphate (SLS) | 0.5 |
| MonoLauryl Phosphate (MLP) | 1.0 |
| triclosan | 0.30 |
| NaF | 0.243 |
| Water | 55.957 |
| Flavor Oil | 1.00 |
| NaOH (25% Sol'n) | 0.5 |
| TOTAL | 100.00 |

The antibacterial activity measured as the antiplaque activity, of Compositions A–F, were assessed using a chemostat plaque system of the type disclosed in the *American Journal of Dentistry*, Vol. 3, Special Issue, September 1990, pages S8–S9. Hydroxyapatite disks were fixed in flow cells connected to a chemostat containing a culture of bacterial growth media having a mixed culture of five species of oral microorganisms (*A. viscosus, S. mutans, S. sanguis, V. parula,* and *F. nucleatum*) associated with human plaque. The culture was pumped through the flow cells at a rate of about 1 ml/minute for 48 hours to grow plaque on the SCHAP disks.

The hydroxyapatite disks were prepared in the following manner:

Hydroxyapatite (HAP) is washed extensively with distilled water, collected by vacuum filtration, and dried overnight at 37° C. The dried HAP is ground into a powder with a mortar and pestle and 150 milligrams (mgs) of the powder is placed into a chamber of a KBr pellet die (Barnes Analytical, Stanford, Conn.). The HAP powder is compressed for 6 minutes at 10,000 pound in a Carver Laboratory press to prepare 13 mm diameter disks which are sintered for 4 hours at 800° C. in a Thermolyne furnace. Parafilm stimulated whole saliva is collected into an ice-chilled glass beaker and the saliva is clarified by centrifugation at 15,000×g (times gravity) for 15 minutes at 4° C. Sterilization of the clarified-saliva is done at 4° C. with stirring by irradiation of the sample with UV light for 1.0 hour.

Each sintered HAP disk is hydrated with sterile water in a polyethylene test tube. The water is then removed and replaced with 2 milliliters (ml) of saliva. A salivary pellicle is formed by incubating the disk overnight at 37° C. with continuous shaking in a water bath to form a saliva coated disk (SCHAP).

To evaluate the antiplaque efficacy of Compositions A–F, each liquid dentifrice was pumped for 30 seconds, at the rate of about 1 ml/minute, through the flow cells containing the SCHAP disks on which the plaque was being grown. A total of four such treatments of the SCHAP disks were given at 12 hour intervals, during a 48 hour plaque growth period. Thereafter, the bacterial plaque grown on the SCHAP disks was removed by immersion of each disk in 2 ml of 0.1 N NaOH solution, in a water bath at 37° C., with gentle shaking for 15 minutes. The disks were removed and the NaOH solution was sonicated to disperse the plaque. The resultant plaque concentration is a function of the turbidity or optical density (O.D.) of the sample, which was determined by measuring the absorbance at 610 nm in a spectrophotometer—the results for Compositions A–F are presented in Table II, below.

TABLE II

Plaque Growth As Measured with Chemostat Plaque System

| Composition | MLP Content<br>(% by Weight) | SLS Content<br>(% by Weight) | Plaque Growth<br>(Spectrometric O.D.) |
|---|---|---|---|
| A | 1.0 | 0.5 | 0.272 |
| B | 0.75 | 0.6 | 0.202 |
| C | 0.75 | 0.75 | 0.284 |
| D | 0.5 | 1.0 | 0.2605 |
| E | 1.5 | 0.0 | 0.3175 |
| F | 0.0 | 1.5 | 0.2943 |

The data recorded in Table II shows that for liquid dentifrice formulations having MLP to SLS ratios of from 2:1 to 1:2, respectively, i.e. Compositions A–D, there is a significant reduction in plaque growth within the chemostat, as compared to compositions in which this ratio was not present, i.e. Compositions E–F.

EXAMPLE II

Using methodology disclosed in the *International Dental Journal*, Vol. 44, Issue No. 1, Supplement 1 (1994), by Gaffar et al., a one cell, single exposure human clinical study was conducted with 5 human subjects to evaluate the effect in vivo of a paste dentifrice, Composition J, of the subject invention (comparable to Composition A of Example I regarding MLP and SLS content). The formulation of paste dentifrice J is presented in Table III, below.

The criteria for the human subjects was an age range of from 18–65, possessing a minimum of 20 uncrowned teeth, and no presence of advanced periodontal disease, extensive untreated dental caries, orthodontic appliances or other diseases of hard or soft oral tissues. Further, any subject using systemic or topical antibiotic drugs or oral antimicrobial mouth rinses or other products containing antimicrobial agents within the period of two weeks prior to the study was excluded.

The subjects were tested at about 8 AM without having eaten or used toothpaste or mouthwash that morning. Prior to the brushing with dentifrice J, a baseline plaque sample was collected from each subject by the dental hygienist, the sample being taken from lingual surfaces of mandibular second molars and buccal surfaces of maxillary canines. The subjects brushed in their usual manner with 1.5 g of dentifrice J for 45 seconds and then rinsed with water. Subsequent to the brushing the subjects were allowed to eat or drink as desired. Plaque samples where collected 6 hours after brushing for assessment of the plaque viability effect of dentifrice J.

The collected baseline and 6 hours after brushing with dentifrice J plaque samples were placed on microscope slides and then treated (within 5 minutes of collection) with 14 ml of a solution of two fluorescent components (ethidium homodimer and 5 chloromethylfluorescein diacetate (available from Molecular Probes Incorporated, Eugene, Oreg.) for 15 minutes at room temperature. After such incubation the slides were tipped slightly to remove any excess dye solution and were rinsed with 100 ml of phosphate buffer saline solution. This treatment resulted in differential staining of live (green stained ) and dead (red stained) bacterial cells. Cover slips were added to the samples and the slides were evaluated at 200× under fluorescent microscopy. Ten different microscope fields of each sample were scored for viable plaque bacteria (or conversely for dead plaque bacteria) using the criteria of Rudegren (see Rudegren, J. Johansson, M., Astrom M., Effect of 4-day Mouth Rinse On Delmopinol as Chlorhexidine on the Viability of Plaque Bacteria, *Journal of Periodontal Dentistry* (1992)). The scoring assigned a numerical value of 1.0 to an all green stain, i.e. 100% viable or 0% dead plaque bacteria; a numerical value of 2.0 to a green with some red, i.e. 25% dead plaque bacteria; a numerical value of 3.0 to green equal to red, i.e. 50% dead plaque bacteria; a numerical value of 4.0 to red with some green, i.e. 75% dead plaque bacteria; and a numerical value of 5.0 to zero green, i.e. 100% dead plaque bacteria. The ten scores were then averaged to obtain a single value for each plaque sample from a single tooth. The data for the four teeth, canines and molars for each subject were then averaged to give a single value for each subject and all five subjects were averaged to obtain a numerical average which was equated to a dead plaque bacteria level for the baseline samples and for the samples taken 6 hours after brushing. The dead plaque bacteria baseline level and 6 hours after brushing level results are recorded in Table IV, below.

For comparison, Experiment II was repeated using a dentifrice having the same formulated as dentifrice J without any MLP and with 1.5% by weight SLS being present (designated Composition K); and also repeated with a commercially available dentifrice advertised as an antiplaque, antibacterial toothpaste (designated Composition L). The dead plaque bacteria baseline level and 6 hours after brushing level results for both comparative Compositions K and L are also recorded in Table IV, below.

TABLE III

Paste Dentifrice Composition J

| Ingredients: | Wt. % |
| --- | --- |
| Glycerine | 20.0 |
| Carageenan | 0.3 |
| NaCMC | 0.8 |
| Propylene Glycol | 0.5 |
| NaF | 0.24 |
| Na Saccharin | 0.3 |
| TiO$_2$ | 0.5 |
| Sorbitol | 20.0 |
| Water (Deionized) | 32.4 |
| NaOH (25% Sol'n) | 0.16 |
| Zeodent 115 | 20.0 |
| Sylodent 15 | 2.0 |
| Triclosan | 0.3 |
| Flavor Oil | 1.0 |
| MLP | 1.0 |
| SLS | 0.5 |
| Total | 100.0 |

TABLE IV

Plaque Bacteria Viability as Measured In Human Clinical Study

| Paste Dentifrice Composition | Baseline Dead Plaque Bacteria Level | Dead Plaque Bacteria Level 6 Hours After Brushing | Percentage Increase In Dead Plaque Bacteria, 6 Hours After Brushing Vs. Baseline |
| --- | --- | --- | --- |
| J | 27.0 +/- 2.5% | 39.5 +/- 5.75% | 46.3% |
| K | 30.6 +/- 3.0% | 37.4 +/- 3.8% | 22.2% |
| L | 29.25 +/- 2.3% | 30.5 +/- 2.1% | 4.3% |

Referring to Table IV, the data for dentifrice Composition J clearly shows a distinct efficacy advantage for the MLP and SLS combination of the present invention in killing plaque bacteria and maintaining the kill over a 6 hour period. The 46.3% increase in dead plaque bacteria observed for Composition J after 6 hours was unexpected, statistically significant, and twice that of comparative Composition K which lacked the presence of MLP. In the case of comparative dentifrice Composition L, the 6 hour dead plaque bacteria level was not statistically different than its observed baseline dead bacteria level, indicating that comparative Composition L was not efficacious against plaque bacteria after 6 hours.

What is claimed is:

1. An oral composition exhibiting increased antibacterial efficacy, the composition comprising in an orally acceptable vehicle; an effective therapeutic amount of a halogenated diphenyl ether or phenolic antibacterial compound; a monoalkyl phosphate compound, which is substantially free of any other alkyl phosphate compound; and another anionic surfactant, other than an alkyl phosphate; the weight ratio of the monoalkyl phosphate to the other anionic surfactant being in the range of about 2:1 to about 1:2.

2. The composition of claim 1, wherein the other anionic surfactant is sodium lauryl sulfate.

3. The composition of claim 1, wherein the oral composition is a paste dentifrice.

4. The composition of claim 1, wherein the antibacterial agent is incorporated in the composition at a concentration of about 0.05 to about 2.0% by weight.

5. The composition of claim 1, wherein the antibacterial agent is triclosan.

6. The composition of claim 1, wherein the monoalkyl phosphate compound is incorporated in the composition at a concentration of about 0.1 to about 5% by weight.

7. The composition of claim 1, wherein the monoalkyl phosphate compound has the formula

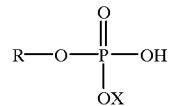

where R is an alkyl or alkenyl group having 6 to 18 carbon atoms and X is hydrogen sodium, potassium or ammonium.

8. The composition of claim 1, wherein the monoalkyl phosphate compound is monolauryl phosphate.

9. The composition of claim 1, wherein the anionic surfactant is incorporated at a concentration of about 0.1 to about 5.0% by weight.

10. The composition of claim 1, wherein the other anionic surfactant is sodium lauryl sulfate incorporated in the composition at a concentration of from about 0.2 to about 3% by weight.

11. A method for the treatment and prevention of bacterial plaque accumulation on teeth which comprises administering to the oral cavity an oral composition, containing an effective therapeutic amount of a hologenated diphenyl ether or phenolic antibacterial compound; a monoalkyl phosphate compound, which is substantially free of any other alkyl phosphate compound; and another anionic surfactant, other than an alkyl phosphate; the weight ratio of the monoalkyl phosphate to the other anionic surfactant being in the range of about 2:1 to about 1:2; wherein, increased antibacterial activity is obtained.

12. The method of claim 11, wherein the other anionic surfactant is sodium lauryl sulfate.

13. The method of claim 11, wherein the oral composition is a paste dentifrice.

14. The method of claim 11, wherein the antibacterial compound is incorporated in the composition at a concentration of about 0.05 to about 2.0% by weight.

15. The method of claim 11, wherein the antibacterial compound is triclosan.

16. The method of claim 11, wherein the monoalkyl phosphate compound is incorporated in the composition at a concentration of about 0.1 to about 5% by weight.

17. The method of claim 11, wherein the monoalkyl phosphate compound has the formula

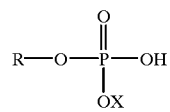

where R is an alkyl or alkenyl group having 6 to 18 carbon atoms and X is sodium, potassium or ammonium.

18. The method of claim 11, wherein the monoalkyl phosphate compound is monolauryl phosphate.

19. The method of claim 11, wherein the anionic surfactant is incorporated at a concentration of about 0.1 to about 5.0% by weight.

20. The method of claim 11, wherein the anionic surfactant is sodium lauryl sulfate incorporated in the composition at a concentration of from about 0.2 to about 3% by weight.

* * * * *